(12) United States Patent
Clarke et al.

(10) Patent No.: US 9,612,183 B2
(45) Date of Patent: Apr. 4, 2017

(54) MODULAR CAPILLARY BRIDGE VISCOMETER

(75) Inventors: Paul G. Clarke, Sandhurst (GB); Michael P. Murphy, West Conroe, TX (US)

(73) Assignee: Malvern Instruments Incorporated, Westborough, MA (US)

( * ) Notice: Subject to any disclaimer, the term of this patent is extended or adjusted under 35 U.S.C. 154(b) by 773 days.

(21) Appl. No.: 13/825,623

(22) PCT Filed: Sep. 23, 2011

(86) PCT No.: PCT/GB2011/051804
§ 371 (c)(1),
(2), (4) Date: Nov. 12, 2013

(87) PCT Pub. No.: WO2012/038761
PCT Pub. Date: Mar. 29, 2012

(65) Prior Publication Data
US 2014/0060162 A1 Mar. 6, 2014

Related U.S. Application Data

(60) Provisional application No. 61/385,955, filed on Sep. 23, 2010.

(51) Int. Cl.
*G01N 11/08* (2006.01)
(52) U.S. Cl.
CPC ................................. *G01N 11/08* (2013.01)
(58) Field of Classification Search
CPC ..................................................... G01N 11/08
(Continued)

(56) References Cited

U.S. PATENT DOCUMENTS

| 3,086,386 A | 4/1963 | Kapff |
| 3,302,448 A | 2/1967 | Mocker |

(Continued)

FOREIGN PATENT DOCUMENTS

| EP | 1707941 | 4/2006 |
| JP | S59160740 | 7/1984 |

(Continued)

*Primary Examiner* — Clayton E Laballe
*Assistant Examiner* — Dennis Hancock
(74) *Attorney, Agent, or Firm* — Kristofer E. Elbing

(57) ABSTRACT

A capillary bridge viscometer (120), comprises at least two at least generally balanced bridge arm conduits (R1, R2) a bulkhead supporting structure (122,134) supporting removable connection portions for each of a plurality of the arms in a bridge configuration, a bridge supporting structure (124,136) supporting the bridge arm conduits (R1,R2) and supporting two further removable connection portions (132) for each of the bridge arm conduits, wherein each of the further removable connection portions (132) supported by the bridge supporting structure are positioned to mate with a corresponding one of the removable connection portions (130) supported by the bulkhead supporting structure concurrently to hydraulically connect the bridge arm conduits in the bridge configuration; and a balance detector having hydraulic connections for connection between first and second differential detection points in the bridge when the removable connection portions on the bridge are mated to corresponding ones of the removable connection portions supported by the bulkhead supporting structure.

17 Claims, 3 Drawing Sheets

(58) Field of Classification Search
USPC .......................................................... 73/54.06
See application file for complete search history.

(56) References Cited

U.S. PATENT DOCUMENTS

| | | | |
|---|---|---|---|
| 4,463,598 A | 8/1984 | Haney | |
| 6,745,615 B2* | 6/2004 | Kensey | A61B 5/02035 |
| | | | 73/54.01 |
| 7,334,457 B2 | 2/2008 | Titterton | |
| 2001/0013248 A1 | 8/2001 | Collin | |
| 2003/0041652 A1* | 3/2003 | Spaid | B01L 3/5027 |
| | | | 73/54.05 |
| 2007/0068229 A1 | 3/2007 | Trainoff | |

FOREIGN PATENT DOCUMENTS

| | | |
|---|---|---|
| JP | 2002527741 | 8/2002 |
| JP | 2006276018 | 12/2006 |
| JP | 2009133726 | 6/2009 |

* cited by examiner

MODULAR CAPILLARY BRIDGE VISCOMETER

This application claims priority to provisional application No. 61/385,955, filed Sep. 23, 2010.

FIELD OF THE INVENTION

The invention relates, in one general aspect, to capillary viscometers, including capillary bridge viscometers with a modular design.

BACKGROUND OF THE INVENTION

Referring to FIG. 1, multi-capillary viscometers can introduce some type of delay unit in order to make a differential measurement while a sample is being measured. An illustrative prior art four-capillary viscometer 10, for example, includes four pieces of tubing or capillaries connected in a series-parallel configuration to form the hydraulic equivalent of a Wheatstone-Bridge in electronics. These tubing or capillaries in the arms of the bridge are often referred to as R1, R2, R3, and R4 because they are in effect hydraulic resistors. The delay unit 102 is placed in series with one of the capillaries and usually it consists of a column packed with or containing a material or solvent that will delay the sample from reaching a reference capillary while a measurement is taking place. This delay unit should generally provide for sufficient time or volume to accommodate the entire elution volume of the analytical GPC (Gel Permeation Chromatography) column set that is used for the separation analysis. In liquid chromatography there are a vast number of column set configurations, many requiring different delay volumes. Initially, the capillary configuration is arranged such that the "bridge" is "balanced" meaning that the DP+ & DP− readings are approximately equal.

In the illustrative viscometer, R1, R2, R3, and R4 are capillary tubes of a small diameter giving them a measurable resistance to the solvent flow, and if R1=R2=R3=R4, the differential pressure (DP) output should theoretically be zero. This is the output signal from the bridge and should be within a small percentage of the total pressure across the bridge measured between the two differential measurement points IP+ and IP when solvent is flowing. This is called the bridge balance and is given by the equation, Balance=4DP/IP−2DP, where DP is the differential signal from the DP+ and DP readings measured in Pascals and IP is as mentioned above measured in Pascals. Capillary 2 bridge viscometers are described in more detail, for example, in U.S. Pat. No. 4,463,598 to Haney, which is herein incorporated by reference.

When a delay volume is placed in series with one or more capillaries, the bridge can be balanced or rebalanced to make up for additional resistance introduced by the presence of the delay volume(s). This can be accomplished by adjusting the length(s) of one or more of the capillary tubing runs to get the bridge balance back to the manufacturing standard balance. Upon installation or during use, it may become necessary to adjust this delay volume according to the analytical column set required or analysis. One or more additional delay volumes of different sizes may therefore be shipped with the instrument or purchased to meet the specific need of the customer. With these changes comes either increased or decreased resistance within the combined capillary and delay column flow path, and the viscometer can be rebalanced by adding or subtracting to the length of the appropriate capillary tubing in order to achieve the most efficient performance by returning to a balanced condition.

The traditional method for balancing a viscometer bridge is to change the length of one or more of the capillary flow paths. This is accomplished by calculating the amount to subtract (or add) from a length of one or more of the capillaries. The bridge is then disassembled to make the change and reassembled by a skilled technician. This can be extremely inconvenient and may also require the instrument to be returned to the manufacturer for qualified servicing. It is also common for the balance to change due to the introduction of different solvents. These changes are typically ignored because of the inconvenience and because the length difference involved can be physically too small to allow an accurate adjustment to be accurately accomplished, and the result can be a decrease in instrument performance.

Referring to FIG. 2, a typical four way connector C makes connections with $\frac{1}{16}$" (1.59 mm) tubing 104. The tubing is pushed completely into a standard fitting 110 before a nut 106 and ferrule 108 are slid into place and tightened securely with a wrench. These can be over-tightened because of leaking or they may become stuck in the fitting, ruining the entire piece of tubing. Improper installation can also result in a space between one end of the tube and the fitting, creating a dead volume which can increase the band broadening of the detector. These connections are considered permanent, although special tools allow the nut and ferrule to be removed if the length needs to be shortened.

SUMMARY OF THE INVENTION

Several aspects of the invention are presented in this application.

According to a first aspect of the invention we provide a capillary bridge viscometer, comprising: at least two at least generally balanced bridge arm conduits, a bulkhead supporting structure supporting removable connection portions for each of a plurality of the arms in a bridge configuration. The bridge viscometer may further comprise a bridge supporting structure supporting the bridge arm conduits and supporting two further removable connection portions for each of the bridge arm conduits. Each of the further removable connection portions may be supported by the bridge supporting structure and are positioned to mate with a corresponding one of the removable connection portions supported by the bulkhead supporting structure concurrently to hydraulically connect the bridge arm conduits in the bridge configuration. The apparatus may include a balance detector having hydraulic connections for connection between first and second differential detection points in the bridge when the removable connection portions on the bridge are mated to corresponding ones of the removable connection portions supported by the bulkhead supporting structure.

The bulkhead may include ports that are positioned to mate with corresponding connectors on the bridge, which supports the bridge conduits. The ports and connectors may define a set of removable connections between the bulkhead and the bridge. The bulkhead may be adapted to act as a pressure plate that provides even pressure on all conduits. The bridge supporting structure may be adapted to be removed and replaced with another bridge supporting structure. A kit of parts may be provided comprising a bulkhead supporting structure and a plurality of bridge supporting structures.

The bulkhead supporting structure may define ports and conduits, which hydraulically connect them to standard fittings that connect to the bridge supporting structure to other parts of the viscometer. The bridge supporting structure may provide the support for the bridge arm conduits while all the remaining conduits and connections for forming the viscometer are provided by the bulkhead supporting structure.

According to a further aspect of the invention, we provide a bulkhead support structure for a capillary bridge viscometer, the bulkhead supporting structure supporting removable connection portions for each of a plurality of the arms in a bridge configuration.

According to a further aspect we provide a bridge supporting structure supporting bridge arm conduits and supporting two further removable connection portions for each of the bridge arm conduits, wherein each of the further removable connection portions supported by the bridge supporting structure are positioned to mate with a corresponding one of the removable connection portions supported by the bulkhead supporting structure concurrently to hydraulically connect the bridge arm conduits in the bridge configuration.

According to a further aspect we provide a balance detector having hydraulic connections for connection between first and second differential detection points in a bridge when the removable connection portions on the bridge are mated to corresponding ones of the removable connection portions supported by the bulkhead supporting structure.

DETAILED DESCRIPTION OF AN ILLUSTRATIVE EMBODIMENT

Figure 1:
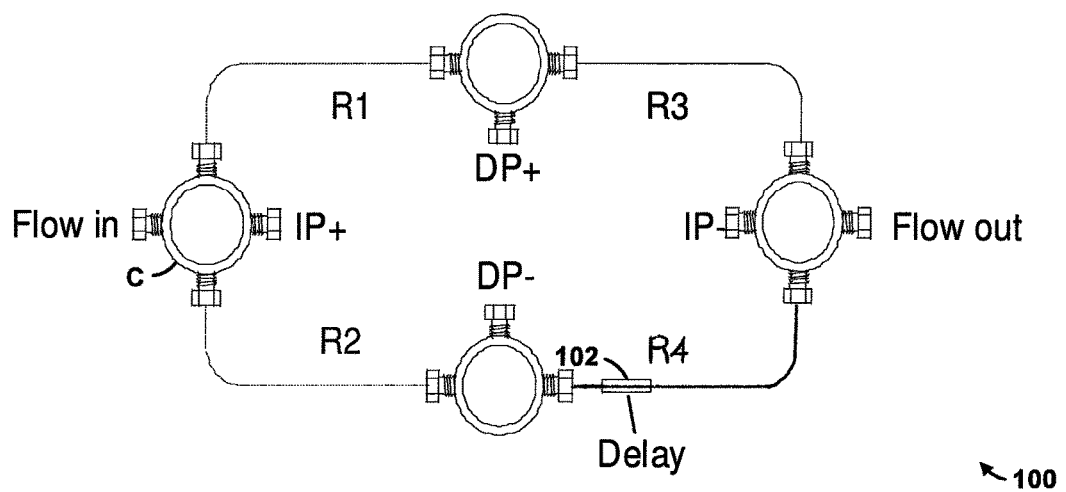
FIG. 1 is a hydraulic schematic diagram of a prior art capillary bridge viscometer.

Referring to FIGS. 3-7, an illustrative capillary bridge viscometer 120 according to the invention includes a bulkhead 122 and a bridge module 124. The bulkhead includes ports 130 that are positioned to mate with corresponding hydraulic connectors 132 on the bridge module, which supports the bridge tubing. The ports and connectors define a set of removable connections between the bulkhead and the bridge module. This arrangement allows the bridge module to be quickly changed for different experiments or if it becomes fouled, and the bridge module can even be disposable.

In the illustrative embodiment, the ports are cylindrical openings in the bulkhead block and the connectors are flangeless low-pressure ferrules, such as are available from IDEX corporation of Lake Forest, Ill. under part number P-200NX. One of ordinary skill would of course recognize that many other suitable types of removable hydraulic fittings could also be used to provide removable connections between the bridge and the bulkhead.

Figure 2:
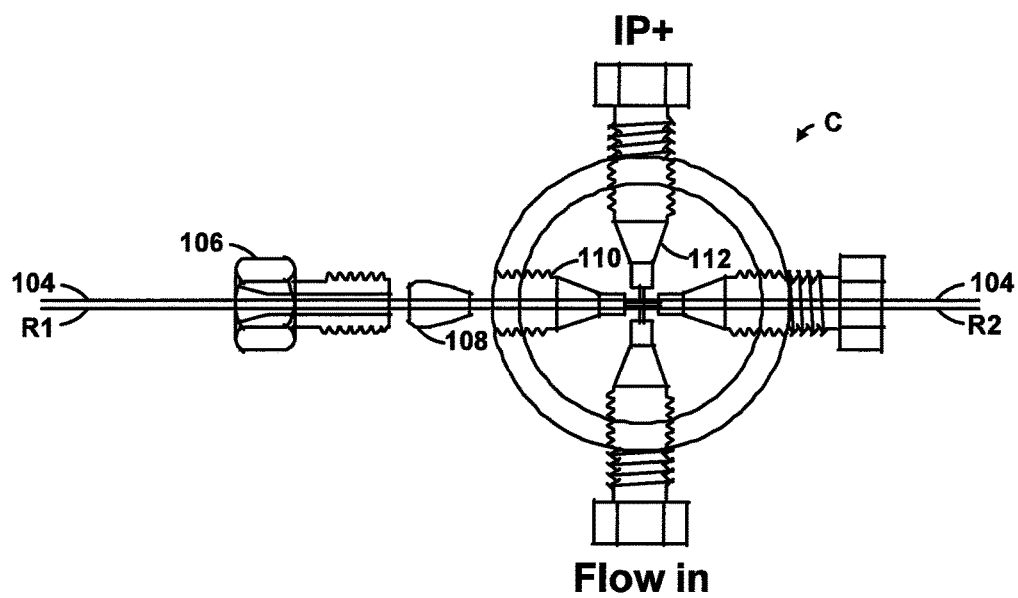
FIG. 2 is a diagram of a typical four-way connector with 1/16" tubing being installed, shown transparently to reveal internal structures.

The bulkhead can be built around a support 134 that defines the ports 130 and conduits 138, which hydraulically connect them to standard fittings that connect the bridge to other parts of the viscometer (e.g., 112 in FIG. 2). The bridge module can also be built around a support 136 that supports the hydraulic connectors 132 and the bridge tubes R1, R2, R3, R4 that they are connected to. In this embodiment, the bulkhead and bridge supports are each made of a machined block of stainless steel, but one of ordinary skill in the art would of course realize that many other suitable materials, construction techniques, and structural configurations could also be used.

A mechanical connection can be provided between the bulkhead and the bridge module. In this embodiment, the mechanical connection can be provided by four common-sized socket head screws that pass through holes 126 in the bridge module support and interact with threaded holes 128 in the bulkhead support. One of ordinary skill would of course recognize that many other suitable types of mechanical connections could also be used.

In operation, the user installs the bridge module 124 on the bulkhead 122 and secures them in place mechanically by tightening the screws. Once tight, the support acts as a pressure plate that provides even pressure on all capillaries and can eliminate the possibility of over-tightening. This installation can take place quickly without risk of confusion.

The user can then run one or more experiments. After that, the bridge module can be removed and replaced with another and further experiments can be conducted. The removed bridge module can be stored, disposed of, cleaned, or returned to the manufacturer for servicing.

Multiple different bridge modules 124 can be provided to be used with the instrument. These different bridges can include different lengths and/or diameters of tubing to allow the viscometer to be used for different applications. The different bridges may also provide other differences in the hydraulic circuits that they provide. For example, the IP+ and IP− points could be made available on the bridge module instead of through the bulkhead, or the bridge module could include a built-in delay mechanism or calibration features. The bridge and bulkhead could also be split into sub-elements.

The bulkhead in the illustrative embodiment has been designed here to yield the equivalent external plumbing connections shown in FIG. 1 with standard HPLC fittings for flow in, flow out, DP+, DP−, and one or more delay columns. With the isolation of the capillaries on the bridge module, the need to remove these external connections would be rare, although only normal effort would be required to do so. The illustrative embodiment can also eliminate dead volume resulting from poor installation of bridge connectors. The illustrative embodiment can use comparable capillaries of comparable lengths and/or diameters to typical existing instruments, but one of ordinary skill in the art would recognize that other lengths and/or diameters may also be used, consistent with distances required to go from port to port.

The modular design described in this application can be used in a variety of different kinds of instruments. It can be used in a more complex capillary viscometer that provides for eliminating break through peaks, for example, such as is described in US Pub. No. 2008/245133 to Titterton, which is herein incorporated by reference. Or it can be used with a mechanically balanced viscometer as provided for in an application entitled BALANCED CAPILLARY BRIDGE VISCOMETER being filed on the same date as this application and herein incorporated by reference. This combination can allow the bridge to be quickly balanced after a new bridge module is connected to the bulkhead. The modular design described in this application can also be used in other types of instruments that can benefit from the ability to make quick changes to precisely dimensioned hydraulic circuitry.

Figure 3:
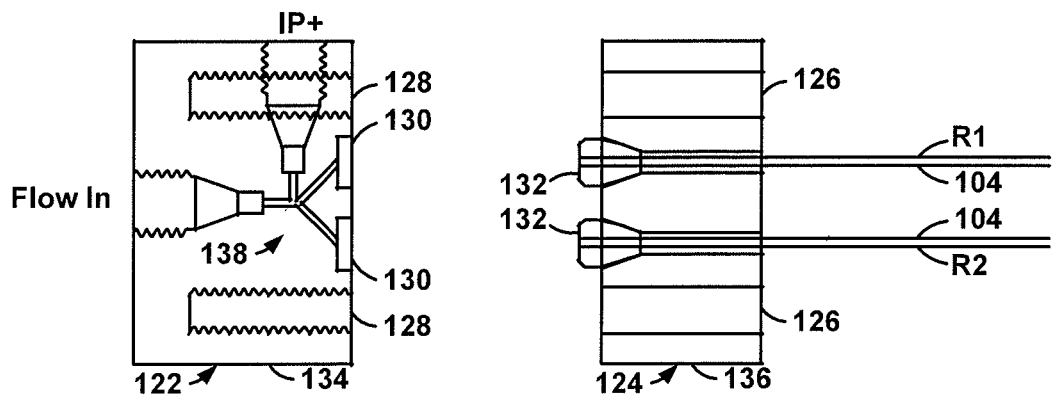
FIG. 3 is a side-view, cross-sectional diagram of an illustrative modular capillary bridge viscometer according to the invention, shown transparently to reveal internal structures.
Figure 4A:
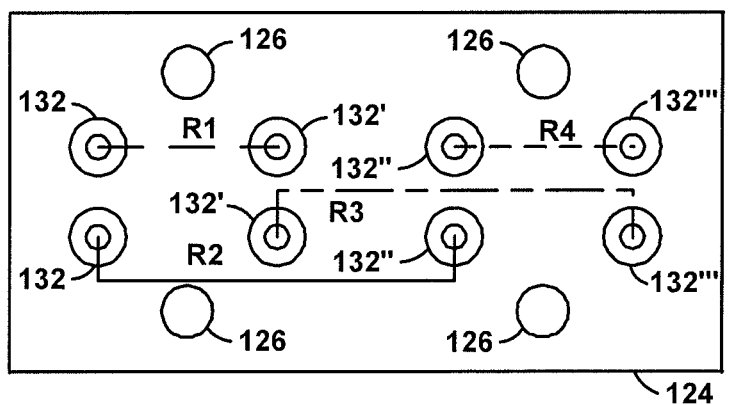
FIG. 4A is a schematic side elevation-view diagram of a bridge module with its conduits shown schematically for the illustrative modular capillary bridge viscometer of FIG. 3.
Figure 7:
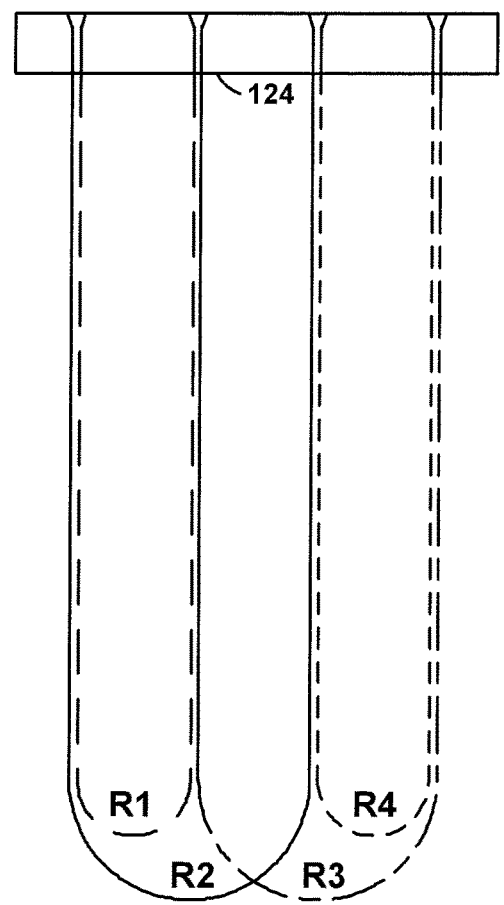
FIG. 7 is a schematic top-view diagram of the bridge module of FIG. 4A.

FIG. 4A shows a schematic side view of the bridge module 124 shown in FIG. 3. Four holes 126 are shown to connect the bridge module 124 to the bulkhead 122. The two hydraulic connectors 132 shown in FIG. 3 are visible on the left hand side of FIG. 4A. The remaining connectors 132', 132", 132''' that provide connections to the other bridge tubes R1, R2, R3 and R4 are positioned in the same face of the bridge module for connection to corresponding ports 130 on the bulkhead 122. FIG. 7 shows a plan view of the path followed by the bridge tubes as represented by the dashed lines in FIG. 4A.

Figure 4B:
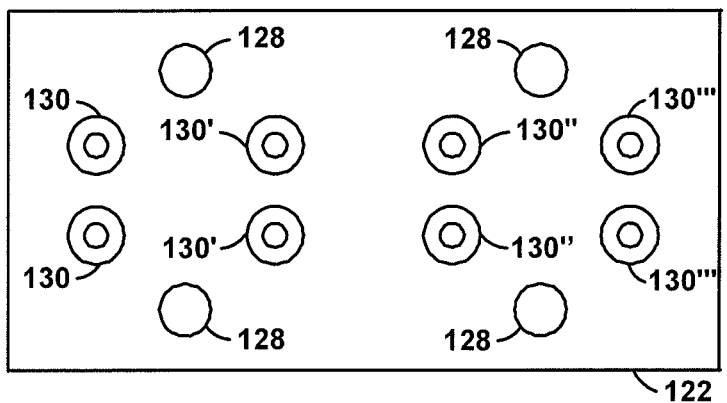
FIG. 4B is a schematic side elevation-view diagram of a bulkhead for the illustrative modular capillary bridge viscometer of FIG. 3.

FIG. 4B shows a similar view to FIG. 4A but on the bulkhead 122. The bulkhead ports 130 are positioned at corresponding positions to the connectors.

Figure 5:
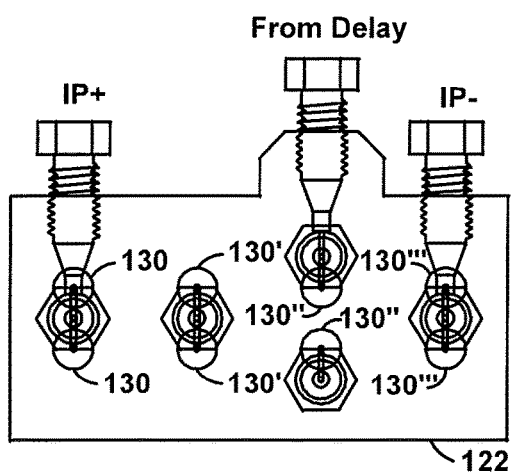
FIG. 5 is a front-view elevation diagram of the bulkhead of FIG. 4B, shown transparently to reveal fittings on the back of the bulkhead.
Figure 6:
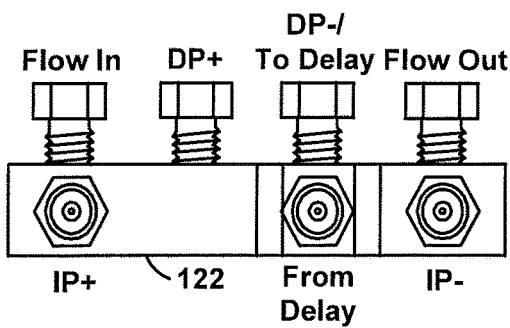
FIG. 6 is a top-view diagram of the bulkhead of FIG. 4B.

FIG. 5 shows a front view of the bulkhead 122 showing the ports IP+, IP− and "From Delay". FIG. 5 shows the bulkhead 122 transparent to make visible the relative positions of the ports 130, 130', 130" and 130''' on the opposite side. FIG. 6 is a top view of the bulkhead 122 to show the ports Flow In, DP+, DP− and Flow Out that are not labelled in FIG. 5 for clarity.

The viscometer 120 may include a balance detector (not shown) which is arranged to correct between the DP+ and DP− ports. The balance detector may include an actuator to adjust the flow rate through viscometer to balance the pressure in the viscometer The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

The invention claimed is:

1. A capillary bridge viscometer, comprising:
   at least two at least generally balanced bridge arm conduits,
   a bulkhead supporting structure supporting removable connection portions for each of a plurality of the arms in a bridge configuration,
   a bridge supporting structure supporting the bridge arm conduits and supporting two further removable connection portions for each of the bridge arm conduits, wherein each of the further removable connection portions supported by the bridge supporting structure are positioned to mate with a corresponding one of the removable connection portions supported by the bulkhead supporting structure concurrently to hydraulically connect the bridge arm conduits in the bridge configuration; and
   a balance detector having hydraulic connections for connection between first and second differential detection points in the bridge when the removable connection portions on the bridge are mated to corresponding ones of the removable connection portions supported by the bulkhead supporting structure.

2. The apparatus of claim 1 wherein the fittings are HPLC fittings.

3. The apparatus of claim 1 or of claim 2 further including an adjustable mechanical flow restrictor in a flow path in one arm of the bridge, wherein the adjustable mechanical flow restrictor is operative to mechanically adjust a resistance to flow of a fluid while the fluid flows through the adjustable mechanical flow restrictor.

4. The apparatus of claim 3 further including an actuator coupled to the adjustable mechanical flow restrictor to adjust the flow rate through the adjustable mechanical flow restrictor.

5. The apparatus of claim 4 wherein the balance detector is operatively connected between first and second differential detection points in the bulkhead supporting structure.

6. The apparatus of claim 5 further including a balancing controller responsive to the balance detector and operative to actuate the actuator to adjust the flow rate through the adjustable mechanical flow restrictor until the capillary bridge viscometer is balanced.

7. The apparatus of claim 1, wherein the balance detector is operatively connected between first and second differential detection points in the bulkhead supporting structure.

8. The apparatus of claim 1 wherein the bulkhead supporting structure includes removable connection portions for each of flow in and flow out.

9. The apparatus of claim 8 wherein the bulkhead supporting structure includes removable connection portions for each of flow in, flow out, and two differential pressure measurement points.

10. The apparatus of claim 9, wherein the balance detector is operatively connected between first and second differential detection points in the bulkhead supporting structure.

11. The apparatus of claim 1, wherein each of the conduits is a capillary tube.

12. The apparatus of claim 1 wherein at least some of the connection portions include ferrules and at least some of the connection portions include ports that are dimensioned to interact with the ferrules.

13. A capillary bridge viscometer, comprising:
   a bulkhead, including:
      a bulkhead support structure,
      an input port,
      a first removable input port fitting hydraulically connected to the input port and mounted with respect to the bulkhead support structure,
      a second removable input port fitting hydraulically connected to the input port and mounted with respect to the bulkhead support structure,
      an output port,
      a first removable output port fitting hydraulically connected to the output port and mounted with respect to the bulkhead support structure,
      a second removable output port fitting hydraulically connected to the output port and mounted with respect to the bulkhead support structure,
      a first detection port,
      a first removable first detection port fitting hydraulically connected to the first detection port and mounted with respect to the bulkhead support structure,
      a second removable first detection port fitting hydraulically connected to the first detection port and mounted with respect to the bulkhead support structure, a first removable input port fitting hydraulically connected to the input port, a second removable input port fitting hydraulically connected to the input port, a second detection port, a first removable second detection port fitting hydraulically connected to the second detection port and mounted with respect to the bulkhead support structure, a second removable second detection port fitting hydraulically connected to the second detection port and mounted with respect to the bulkhead support structure, and a bridge, including:

a bridge support structure, a first conduit having first and second removable fittings that are mounted with respect to the bridge support structure, a second conduit having first and second removable fittings that are mounted with respect to the bridge support structure, a third conduit having first and second removable fittings that are mounted with respect to the bridge support structure, a fourth conduit having first and second removable fittings that are mounted with respect to the bridge support structure, wherein the fittings in the bridge and the fittings on the bulkhead are positioned to allow concurrent connection of:

the first removable fitting of the first conduit to the first removable input port fitting, the second removable fitting of the first conduit to the first removable first detection port fitting, the first removable fitting of the second conduit to the second removable first detection port fitting, the second removable fitting of the second conduit to the first removable output port fitting, the first removable fitting of the third conduit to the second removable input port fitting, the second removable fitting of the third conduit to the first removable second detection port fitting, the first removable fitting of the fourth conduit to the second removable second detection port fitting, and the second removable fitting of the fourth conduit to the second removable output port fitting.

14. The apparatus of claim 13 wherein each of the conduits is a capillary tube.

15. The apparatus of claim 1 wherein the bulkhead supporting structure comprises a bulkhead, including an input port, an output port, a first detection port, a second detection port and wherein the bulkhead includes;

a first removable input port fitting hydraulically connected to the input port an mounted with respect to the bulkhead support structure, a second removable input port fitting hydraulically connected to the input port and mounted with respect to the bulkhead support structure, a first removable output port fitting hydraulically connected to the output port and mounted with respect to the bulkhead support structure, a second removable output port fitting hydraulically connected to the output port and mounted with respect to the bulkhead support structure, a first removable first detection port fitting hydraulically connected to the first detection port and mounted with respect to the bulkhead support structure, a second removable first detection port fitting hydraulically connected to the first detection port and mounted with respect to the bulkhead support structure, a first removable second detection port fitting hydraulically connected to the second detection port and mounted with respect to the bulkhead support structure, and a second removable second detection port fitting hydraulically connected to the second detection port and mounted with respect to the bulkhead support structure.

16. The apparatus of claim 1 wherein the bridge supporting structure comprises a bridge, including:

a first conduit having first and second removable fittings that are mounted with respect to the bridge support structure, a second conduit having first and second removable fittings that are mounted with respect to the bridge support structure, a third conduit having first and second removable fittings that are mounted with respect to the bridge support structure, a fourth conduit having first and second removable fittings that are mounted with respect to the bridge support structure, wherein the fittings in the bridge and the fittings on the bulkhead are positioned to allow concurrent connection of:

the first removable fitting of the first conduit to the first removable input port fitting, the second removable fitting of the first conduit to the first removable first detection port fitting, the first removable fitting of the second conduit to the second removable first detection port fitting, the second removable fitting of the second conduit to the first removable output port fitting, the first removable fitting of the third conduit to the second removable input port fitting, the second removable fitting of the third conduit to the first removable second detection port fitting, the first removable fitting of the fourth conduit to the second removable second detection port fitting, and the second removable fitting of the fourth conduit to the second removable output port fitting.

17. The apparatus of claim 15 or claim 16 wherein each of the conduits is a capillary tube.

* * * * *